(12) United States Patent
Nishimura et al.

(10) Patent No.: US 7,332,624 B2
(45) Date of Patent: Feb. 19, 2008

(54) METHOD FOR PRODUCTION OF ACRYLIC ACID

(75) Inventors: Takeshi Nishimura, Himeji (JP); Yukihiro Matsumoto, Kobe (JP); Kenji Sanada, Himeji (JP); Harunori Hirao, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 10/607,767

(22) Filed: Jun. 27, 2003

(65) Prior Publication Data
US 2004/0015014 A1     Jan. 22, 2004

(30) Foreign Application Priority Data
Jul. 16, 2002  (JP) .............................. 2002-206707

(51) Int. Cl.
*C07C 51/16* (2006.01)
*C07C 51/42* (2006.01)

(52) U.S. Cl. ...................... 562/532; 562/545; 562/549; 562/600

(58) Field of Classification Search ............... None
See application file for complete search history.

(56) References Cited

U.S. PATENT DOCUMENTS

| 4,317,926 | A | 3/1982 | Sato et al. ............... 562/532 |
| 5,785,821 | A | 7/1998 | Sakamoto et al. | |
| 6,252,110 | B1 * | 6/2001 | Uemura et al. ........... 562/598 |
| 6,409,886 | B1 * | 6/2002 | Matsumoto et al. ........ 203/8 |

FOREIGN PATENT DOCUMENTS

| DE | 100 64 641 A1 | 12/2000 |
| JP | A-9-157213 | 6/1997 |
| JP | 09-295958 | 11/1997 |
| JP | A-10-120618 | 5/1998 |
| JP | A-11-12222 | 1/1999 |
| JP | A-2000-355570 | 12/2000 |

OTHER PUBLICATIONS

The Kirk-Othmer Encyclopedia of Chemical Technology, pp. 342-369, Copyright © 1991 by John Wiley & Sons, Published Online: Dec. 4, 2000 (Kirk Othmer).*
Decision of Rejection issued by the Japanese Patent Office citing Ref. 1: JP-A-11-012222 (equivalent to U.S. Patent No. 6,252,110); Ref. 2: JP-A-09-295958 (Abstract in English is attached); Ref. 3: JP-A-2000-355570 (equivalent to U.S. Patent No. 6,409,886) and Ref. 4: JP-A-10-120618 (partial translation filed Sep. 11, 2006).
Communication pursuant to Article 96(2) EPC in corresponding European Patent Application No. 03 254 653.3-1211 dated Feb. 22, 2007.

* cited by examiner

*Primary Examiner*—Karl Puttlitz
(74) *Attorney, Agent, or Firm*—Mathews, Shepherd, McKay & Bruneau, PA

(57) ABSTRACT

A method for the production of acrylic acid comprises (i) a step for introducing a polymerization inhibitor to a stage other than a stage for supplying a raw material and a stage for supplying a reflux of said distilling column or (ii) a step for supplying the acrylic acid recovered by thermally decomposing said oligomer to said stage for dehydration. Thus, the present invention enjoys effective utilization of acrylic acid and exalts the efficiency of production.

11 Claims, 1 Drawing Sheet

METHOD FOR PRODUCTION OF ACRYLIC ACID

BACKGROUND OF THE INVENTION

1. Field of the Invention

This invention, in a method for the production of acrylic acid comprising steps for absorbing with water an acrylic acid-containing gas obtained by the reaction of catalytic gas phase oxidation, removing low boiling substances and high boiling substances, and a step for thermally decomposing an acrylic acid oligomer contained in the high boiling substance-containing solution obtained in the step for removal, relates to a method for the production of acrylic acid which allows to prevent the polymerization more efficiently and enjoys exalted productivity.

2. Description of the Related Art

Acrylic acid is used in coating, textile processing, leather products, and building materials, as well as for copolymers destined to produce acrylic fibers and for emulsions to produce tackiness agents and adhesive agents. The demand for acrylic acid is now increasing. With a view to realizing mass production of acrylic acid by using an inexpensive raw material, therefore, it is common for acrylic acid to be produced by the reaction of catalytic gas phase oxidation of propylene, for example. Since the reaction of catalytic gas phase oxidation gives rise to by-production of low boiling substances and high boiling substances besides yielding acrylic acid, various processes are relied on to separate and remove such by-products and purify acrylic acid.

The official gazette of JP-A-09-157213, for example, discloses a method for producing acrylic acid by introducing a mixed gas obtained by the catalytic gas phase oxidation of propylene, for example, to an acrylic acid absorption column, causing the gas to contact an aqueous absorbing solvent containing acrylic acid, acetic acid, and sparingly water-soluble solvent thereby obtaining an aqueous acrylic acid solution, dehydrating the aqueous acrylic acid solution in an azeotropic separation column and obtaining through the bottom of this column acrylic acid substantially free from acetic acid, water, and sparingly water-soluble solvent, meanwhile expelling through the top of the column a mixture consisting of acetic acid, acrylic acid, water, and sparingly water-soluble solvent by distillation, separating the expelled mixture in a storage tank into an organic phase formed substantially of a solvent and a water phase formed of acrylic acid, acetic acid, a solvent, and water, and circulating the organic phase in the azeotropic separation column.

The solution, the exhaust gas, and the like which emanate from such purification processes possibly contain raw material compounds, produced compounds, and other useful compounds. With the object of exalting the efficiency of production, the practice of putting these materials to circulatory use in the process of production is continuing in use.

The official gazette of JP-A-11-012222, for example, discloses a method for recovering acrylic acid from acrylic acid containing acrylic acid dimer and maleic acid, which is characterized by introducing the acrylic acid containing acrylic acid dimer and maleic acid into an acrylic acid-recovering column, expelling acrylic acid by distillation through the top of the column to recover the acrylic acid, meanwhile introducing the bottom liquid (A) from the acrylic acid-recovering column into a thermal decomposition tank and decomposing the acrylic acid dimer in the bottom liquid (A), and then circulating at least part of the bottom liquid (B) from the thermal decomposition tank to the acrylic acid-recovering column. This method is directed toward effective use of the acrylic acid dimer and maleic acid and, by circulating the acrylic acid produced by the decomposition to an acrylic acid-recovering column, is enabled to obtain acrylic acid as a finished product.

Acrylic acid is an easily polymerizing compound and is liable to generate an acrylic acid polymer during the process for absorption of acrylic acid and the subsequent process for purification. Various purification columns, therefore, have been used to produce acrylic acid while preventing the occurrence of polymerization by adjusting distillation pressure, temperature, feed rates of liquids, and the like.

The official gazette of JP-A-2000-355570, for example, discloses a method for distilling an easily polymerizing compound by the use of a distilling device, specifically a method for preventing an easily polymerizing compound from being polymerized, characterized by supplying a liquid substantially identical in composition with the liquid existing in the periphery of component member disposed in the distilling device to the component member by an introducing means by spray. The concept of spraying a liquid substantially identical in composition with the liquid existing in the periphery of component member throughout the entire surface of the component member has originated in the discovery that an easily polymerizing compound begins to polymerize when it is left stagnating on the surface of a component member inside a distilling device and the subsequent discovery that the polymerization within the distilling device would be effectively prevented by performing distillation while allowing no stagnation of the liquid on the surface of the component member in the distilling device. The term "liquid identical in composition" as used herein embraces a feed liquid, a liquid extracted from the interior of the column, a reflux, and a circulating liquid of bottoms (a purified liquid). This liquid diluted to a low concentration with water, alcohol, azeotropic solvent, or extracting solvent can also be used.

Since acrylic acid is an easily polymerizing compound, however, the process for the absorption of acrylic acid and the subsequent process for purification are liable to form acrylic acid polymers. Various purification columns have been used to produce acrylic acid while preventing the occurrence of polymerization by adjusting distilling pressure, temperature, and amount of feed liquid. The control of these factors is not easy because the pressure and the concentration change simultaneously with a change in temperature. The occurrence of an acrylic acid polymer results in lowering the yield of the product.

In the process for the purification of acrylic acid, not only the acrylic acid polymer but also by-products generated by the reaction of catalytic gas phase oxidation adheres to such devices as the distilling column and the occurrence of this adherence entails such harmful effects as blocking the devices and possibly impairs lasting stable production of acrylic acid.

In the high boiling substance-containing solution resulting from the separation of high boiling substances, the so-called Michael type adduct of acrylic acid exists besides the acrylic acid dimer and forms a cause for degrading the efficiency of raw material for the process of acrylic acid production. When the Michael type adduct accumulates in the process, it inflicts a serious hindrance on the process for purification and the process of production as well and entails elevation of temperature and formation of by-products possibly to the extent of degrading the quality of product. When such compounds are recovered as acrylic acid, the recovery possibly results in degrading the quality of acrylic acid.

SUMMARY OF THE INVENTION

The present inventor has discovered that in a method for the production of acrylic acid which comprises absorbing in water the acrylic acid-containing gas obtained by the reaction of catalytic gas phase oxidation, separating a low boiling substance, separating a high boiling substance, and thermally decomposing an acrylic acid oligomer, the efficiency of production of acrylic acid can be improved by effecting either (i) a step for introducing a polymerization inhibitor to a stage other than a stage for supplying raw material(what is called "step for feeding") to a distilling column and a stage for supplying a reflux thereto, or (ii) a step for supplying to a step for dehydration the acrylic acid recovered by thermal decomposition of the oligomer. The method for producing the acrylic acid may incorporate therein a step for producing an acrylic ester from the produced acrylic acid or a step for further purifying the produced acrylic acid into acrylic acid of a higher purity. It may further incorporate therein a step for producing a polyacrylic acid (or salt thereof) by using the acrylic acid of a high purity mentioned above.

This invention, particularly by providing a tank and/or a cooler between each the step for absorption in water, the step for separation of low boiling substances, the step for separating high boiling substances, and the step for thermal decomposition of the acrylic acid oligomer, cooling the feeds to the subsequent steps, and then performing the subsequent steps, prevents the occurrence of polymers to the subsequent steps and exalts the eventual yield of production.

This invention, in the method for the production of acrylic acid which comprises steps for absorbing in water the acrylic acid-containing gas resulting from the reaction of catalytic gas phase oxidation, removing low boiling substances and high boiling substances, and thermally decomposing the acrylic acid oligomer contained in the high boiling substance-containing solution resulting from the step for removal, can prevent the polymerization more efficiently and exalt the productivity.

DESCRIPTION OF THE PREFERRED EMBODIMENT(S)

Figure 1:
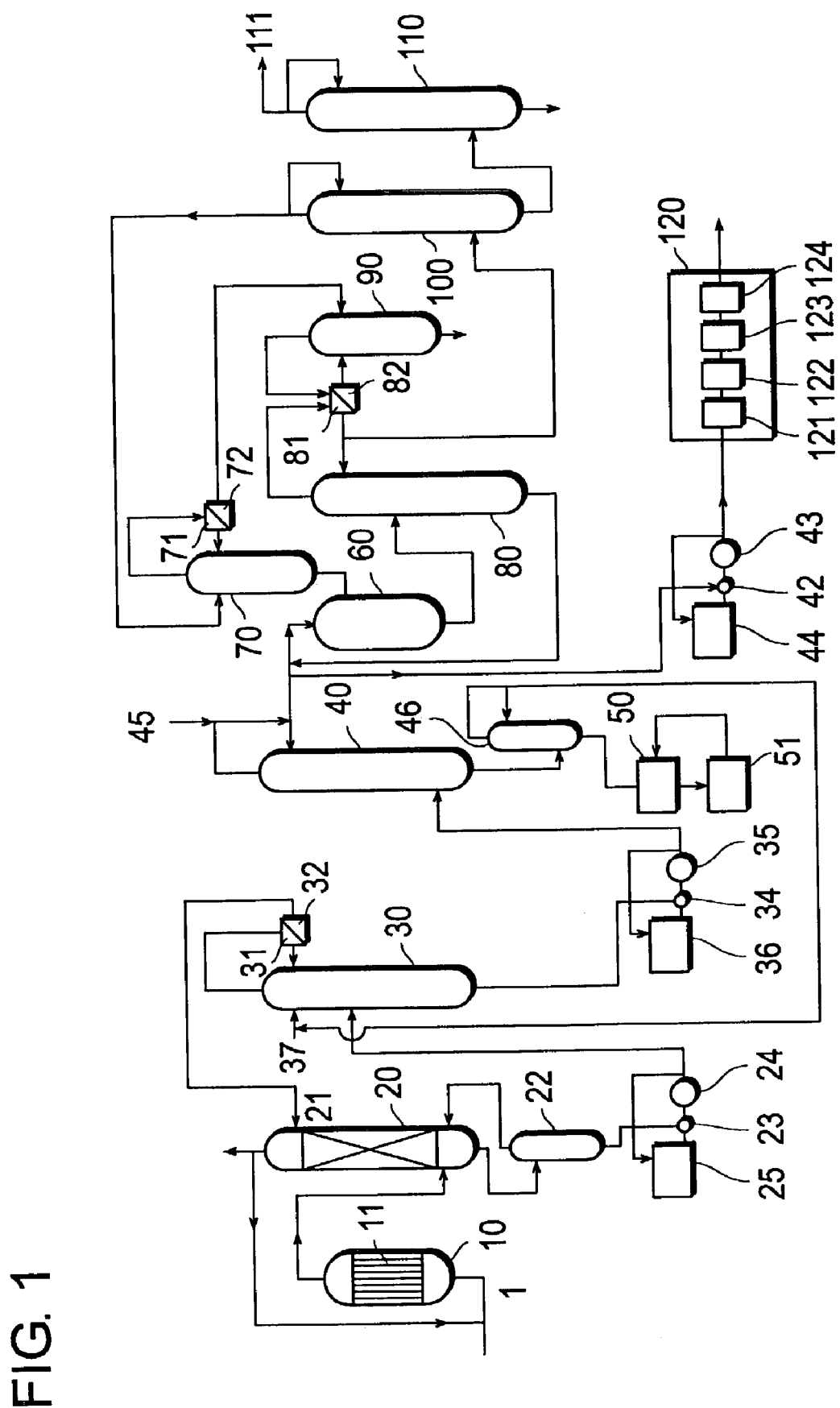
FIG. 1 is a flow diagram illustrating schematically a process for the production of acrylic acid including a step for the production of an acrylic ester and a process for the production of polyacrylic acid (salt).

The first aspect of this invention relates to a method for the production of acrylic acid which comprises (a) a step for obtaining an acrylic acid-containing gas by catalytic gas phase oxidation, (b) a step for obtaining an aqueous acrylic acid-containing solution by absorbing the acrylic acid-containing gas with an aqueous absorbing solvent, (c) a step for obtaining crude acrylic acid by dehydration and/or removing low boiling substance from said aqueous acrylic acid-containing solution, (d) a step for obtaining acrylic acid and high boiling substance-containing solution by removing high boiling substances from the crude acrylic acid, and (e) a step for recovering acrylic acid by thermally decomposing the acrylic acid oligomer contained in the high boiling substance-containing solution, which method is characterized by performing at least either of (i) a step for introducing a polymerization inhibitor to a stage other than the stage for supplying a raw material and the stage for supplying a reflux to the distilling column or (ii) a step for supplying the acrylic acid recovered by thermally decomposing the oligomer to the step for obtaining crude acrylic acid by dehydration.

The term "low boiling substance" as used in this invention refers to as a substance having a lower boiling point than acrylic acid under standard conditions and the term "high boiling substance" refers to as a substance having a higher boiling point than acrylic acid under standard conditions.

The term "acrylic acid oligomer" refers to the Michael type adduct of acrylic acid which is represented by the following formula [I].

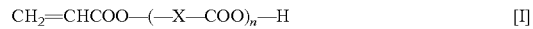

$$CH_2=CHCOO-(-X-COO)_n-H \quad [I]$$

(wherein n is an integer of 1-5 and —X— stands for —CH$_2$CH$_2$— or —CH(CH$_3$)—, providing that the plurality of —X—'s may be identical or different where n is 2 or more.)

The term "polyacrylic acid (salt)" refers to as a polymer containing acrylic acid and/or an acrylic acid salt as the main component of the monomer thereof, more specifically in a ratio of not less than 70 mol %, more preferably not less than 90 mol %, and most preferably substantially 100 mol %. By using such polyacrylic acid (salt), it is made possible to produce a water-soluble polyacrylic acid (salt) and a water-absorbent resin. As the polyacrylic acid salts, preferably univalent salts and more preferably alkali metal salts and ammonium salts may be cited. Such acrylic acid may be copolymerized with other monomer. For example, the acrylic acid (salt) monomer may be either cross-linked with approximately 0.01-5 mol % (based on the acrylic acid) of a cross-linking agent or graft polymerized to such other hydrophilic polymer as starch and polyvinyl alcohol. The term "water-soluble polymer" used herein refers to as such a polymer as exhibits solubility of substantially 100% in water. The term "water-absorbent resin" used herein refers to as such a polyacrylic acid (salt) as possesses a cross-linked structure and exhibits a property of swelling with water and water-insolubility.

The term "distilling column" as used in this invention embraces a wide range of devices, regardless of designations, such as collecting column, absorbing column, dehydrating column, azeotropic dehydrating column, low boiling substance separating column, high boiling substance separating column, acetic acid separating column, purifying column, and thin-film evaporator, which are used for separating components by virtue of difference in boiling point.

The term "purifying" embraces distillation, stripping, crystallization, extraction, and absorption, for example. The term "distillation" means a method for separating volatile components contained in a solution by heating the solution to its boiling point, the term "stripping" refers to as a method for transferring a target substance in a solution to a gas phase by supplying a stripping gas into the solution. The term "crystallization" means a method for separating a target substance in the form of crystals.

One example of the preferred mode of embodying this invention will be described below with reference to FIG. 1.

The method of this invention for the production of acrylic acid comprises supplying a raw material gas 1 containing raw material component, inert gas, molecular oxygen, steam, and the like to a reactor 10 for catalytic gas phase oxidation and subjecting the raw material to the reaction of catalytic gas phase oxidation with a molecular oxygen-containing gas. Specifically, the raw material gas is supplied to the reactor 10 such as, for example, a shell-and-tube type reactor packed with an oxidizing catalyst 11. The oxidation of propylene as a raw material component, for example, results in forming acrolein. The acrolein, when further subjected to the reaction of catalytic gas phase oxidation, produces acrylic acid. The reaction conditions such as raw material gas, oxidizing catalyst, inert gas, molecular oxygen-containing gas, and reaction temperature which are used for this production of acrylic acid may be any of the sets of conditions which are used in the heretofore known processes for the reaction of acrylic acid.

The raw material gas is composed of 1 to 15 vol. % of such a raw material component as one or more of propylene, propane, and acrolein, 1 to 3 times the amount of the raw material components a of a molecular oxygen, and the balance of such inert gas as carbon dioxide or steam. Though the reactor for performing the reaction of catalytic gas phase oxidation does not need to be particularly restricted, a shell-and-tube type reactor can be used advantageously in respect that it excels in the efficiency of reaction. The acrylic acid is produced by the one-stage reaction when acrolein is used as the raw material component or by the so-called two-stage reaction of catalytic gas phase oxidation when propylene is used as the raw material component. The former-stage catalyst and the latter-stage catalyst to be used in the two-stage reaction of catalytic gas phase oxidation do not need to be particularly restricted.

The former-stage catalyst is required to produce acrolein from propylene. As typical examples of this catalyst, those represented by the general formula: $Mo_a$—$Bi_b$—$Fe_c$-$A_d$-$B_e$-$C_f$-$D_g$-$O_x$ (wherein Mo, Bi, and Fe respectively stand for molybdenum, bismuth, and iron, A stands for at least one element selected from the group consisting of nickel and cobalt, B stands for at least one element selected from the group consisting of alkali metals and thallium, C stands for at least one element selected from the group consisting of phosphorus, niobium, manganese, cerium, tellurium, tungsten, antimony, and lead, D stands for at least one element selected from the group consisting of silicon, aluminum, zirconium, and titanium, O stands for oxygen, a, b, c, d, e, f, g, and x respectively represent atomic ratios of Mo, Bi, Fe, A, B, C, D, and O such that $b=0.1-10$, $c=0.1-10$, $d=2-20$, $e=0.001-5$, $f=0-5$, and $g=0-30$ are satisfied when $a=12$ is fixed, and x assumes a numerical value which will be fixed by the oxidizing states of the relevant elements) may be cited.

The latter-stage catalyst is required to effect gas phase oxidation of a reaction gas containing acrolein to produce acrylic acid. As typical examples of this catalyst, those represented by the general formula: $Mo_a$—$V_b$—$W_c$—$Cu_d$-$A_e$-$B_f$-$C_g$-$O_x$, (wherein Mo stands for molybdenum, V stands for vanadium, W stands for tungsten, Cu stands for copper, A stands for at least one element selected from the group consisting of antimony, bismuth, tin, niobium, cobalt, iron, nickel, and chromium, B stands for at least one element selected from the group consisting of alkali metals, alkaline earth metals, and thallium, C stands for at least one element selected from the group consisting of silicon, aluminum, zirconium, and cerium, O stands for oxygen, a, b, c, d, e, f, g, and x respectively represent atomic ratios of Mo, V, W, Cu, A, B, C, and O such that $b=2-14$, $c=0-12$, $d=0.1-5$, $e=0-5$, $f=0-5$, and $g=0-20$ are satisfied when $a=12$ is fixed, and x represents a numerical value which is fixed by the oxidizing states of the relevant elements) may be cited. The acrylic acid-containing gas which is obtained from the reactor 10 generally contains 10-20 wt. % of acrylic acid, 0.2-1.0 wt. % of acetic acid, and 5-15 wt. % of water.

The acrylic acid-containing gas which is obtained by the reaction of catalytic gas phase oxidation is supplied to an acrylic acid absorbing column 20. The process which ensues therein is directed to absorbing the acrylic acid contained in the gas obtained by the process for reaction with an aqueous absorbing solvent. The reaction conditions such as the composition of gas components in the reaction gas, the composition of the aqueous absorbing solvent, and the temperature of the absorption which are used for this process may be any of the sets of conditions which are used in the heretofore known processes for the reaction of acrylic acid. When the acrylic acid-containing gas contains unaltered acrolein, the acrylic acid-containing gas may be supplied to the acrylic acid absorbing column 20 after the acrolein has been removed as by distillation or diffusion. It may be otherwise supplied to the absorbing column 20 after the gas has been cooled. This is because the degree with which the absorption efficiency is exalted increases in accordance as the gas temperature is lowered.

The absorbing column 20 to be used herein may be any of such known absorbing columns as plate column, packed column, wetted wall tower, and spray tower. Generally, this absorbing column 20 is preferred to be a plate column or a packed column. In the case of the packed column, the interior thereof is packed regularly or irregularly with a filler having a large surface are a and exhibiting air permeability. The gas-liquid contact is effected on the surface of the packed bed filled with the filler.

In the absorbing column 20, while the acrylic acid-containing gas is introduced thereto, an absorbing solvent 21 capable of absorbing acrylic acid is introduced from the upper part into this column to bring into counter current contact with the gas mentioned above and to effect absorption of acrylic acid.

As the absorbing solvent 21 so supplied, an aqueous absorbing solvent may be used. This solvent is at an advantage in being inexpensive and allowing exhaust water emanating from the process for the production of acrylic acid to be reused. The aqueous absorbing solvent is only required to contain at least 80-100 wt. % of water. One example of such an aqueous absorbing solvent may be composed of 0.1-5.0 wt. % of acrylic acid, 0.1-10 wt. % of acetic acid, and 80-99.8 wt. % of water. The absorbing solvent 21 to be used herein may be prepared in advance as formulated in the composition mentioned above. For example, a water phase in an oil-water separator 32 annexed to an azeotropic dehydrating column 30 may be circulated as the absorbing solvent 21 for acrylic acid to an acrylic acid absorbing column and used as such.

The absorption efficiency of the absorbing solvent 21 increases in accordance as the solvent temperature decreases. The absorbing solvent 21 is preferred to be supplied at a fixed temperature in the range of 0-35° C., particularly 5-30° C. The amount of the solvent expressed in the liquid-gas ratio, namely the amount of the solvent (L) to the amount of the feed gas ($m^3$), is set in the range of 2-15 L/$m^3$, preferably 3-12 L/$m^3$, and more preferably 5-10 L/$m^3$. The polymerization of acrylic acid occurs most readily when the mass ratio of acrylic acid and water is approximately 50:50. The absorption of acrylic acid can be effected efficiently by maintaining the mass ratio in the range mentioned above and preventing the polymerization.

This invention, for the purpose of preventing the polymerization of such a polymerizing substance as acrylic acid, prefers the absorbing solvent 21 to contain therein at least one compound selected from the group consisting of N-oxyl compounds, phenol compounds, manganese salts such as manganese acetate, copper dialkyldithiocarbamates such as copper dibutylthiocarbamate, nitroso compounds and amine compounds, and phenothiazine. The nitroso compound includes such compounds as N-nitrosophenyl hydroxyl amines or the salts thereof, for example, ammonium salts of N-nitrosophenyl hydroxylamine, p-nitrosophenol, N-nitrosodiphenyl amine and ammonium salts thereof which are decomposed by the conditions of the distilling column and the decomposed components thereof manifest an effect of inhibiting polymerization of easily polymerizing substance. The polymerization inhibitor which is contemplated by the present invention does not embrace such a substance as undergoes decomposition in the distilling column and gives such a product of decomposition as manifests an effect of inhibiting polymerization.

The N-oxyl compound does not need to be particularly restricted. Any of the N-oxyl compounds which have been generally known heretofore as agents for inhibiting the polymerization of a vinyl compound may be used. Among other such N-oxyl compounds, 2,2,6,6-tetramethyl piperidinoxyls represented by the following formula (1):

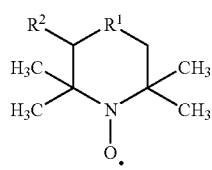

(1)

(wherein $R^1$ stands for $CH_2$, CHOH, $CHCH_2OH$, $CHCH_2CH_2OH$, $CHOCH_2OH$, $CHOCH_2CH_2OH$, CHCOOH, or C=O and $R^2$ stands for a hydrogen atom or $CH_2OH$) are used advantageously. It is preferable to use one or more compounds selected among 2,2,6,6-tetramethyl piperidinoxyl, 4-hydroxy-2,2,6,6-tetramethylpiperidinoxyl, and 4,4',4"-tris-(2,2,6,6-tetramethyl piperidinoxyl) phosphites which give good effects in preventing polymerization, although any of N-oxyl compounds can be used without any limitation. Particularly when 2,2,6,6-tetramethyl piperidinoxyl or 4-hydroxy-2,2,6,6-tetramethyl piperidinoxyl is used as the N-oxyl compound, since it forms a stabilizing agent without requiring to include any metal in the components, there is no possibility of corroding the metallic material of the equipment due to the presence of stabilizer and the waste liquid can be easily treated.

In this invention, the N-oxyl compound may be used in combination with an N-hydroxy-2,2,6,6-tetramethyl piperidine compound and a 2,2,6,6-tetramethyl piperidine compound.

As representative examples of the N-hydroxy-2,2,6,6-tetramethyl piperidine compound, 1,4-dihydroxy-2,2,6,6-tetramethyl piperidine and 1-hydroxy-2,2,6,6-tetramethyl piperidine may be cited. These N-hydroxy-2,2,6,6-tetramethyl piperidine compounds may be used either singly or in the form of a mixture of two or more members.

As typical examples of the 2,2,6,6-tetramethyl piperidine compound. 2,2,6,6-tetramethyl piperidine and 4-hydroxy-2,2,6,6-tetramethyl piperidine may be cited. These may be used either singly or in the form of a mixture of two or more members. Incidentally, N-hydroxy-2,2,6,6-tetramethyl piperidine compounds and 2,2,6,6-tetramethyl piperidine compounds are possibly contained as impurities in commercially available products of N-oxyl compounds. The use of such a commercially available product of N-oxyl compound equals the use in combination with N-hydroxy-2,2,6,6-tetramethyl piperidine compound and 2,2,6,6-tetramethyl piperidine compound mentioned above.

As typical examples of the phenol compound, hydroquinone, methoquinone (p-methoxy-phenol) may be cited. The methoquinone proves favorable in respect that it excels the hydroquinone in the effect of preventing polymerization when it is used in combination with an N-oxyl compound and a phenothiazine compound. These phenol compounds may be used in the form of a mixture of two or more members.

As typical examples of the phenothiazine compound, phenothiazine, bis-(α-methylbenzyl)phenothiazine, 3,7-dioctylphenothiazine, and bis-(α-dimethylbenzyl)phenothiazine may be cited.

The copper salt compound does not need to be particularly restricted. Either copper inorganic salts or copper organic salts can be used. As typical examples, copper dialkyldithiocarbamates, copper acetate, copper napthenate, copper acrylate, copper sulfate, copper nitrate, and copper chloride may be cited. These copper salt compounds are usable in the form of monovalent or divalent compounds. Among other copper salt compounds mentioned above, copper dialkyldithiocarbamates prove favorable from the viewpoint of effect.

As typical examples of the copper dialkyldithiocarbamate, copper dimethyldithiocarbamate, copper diethyldithiocarbamate, copper dipropyldithiocarbamate, copper dibutyldithiocarbamate, copper dipentyldithiocarbamate, copper dihexyldithiocarbamate, copper diphenyldithiocarbamate, copper methylethyldithiocarbamate, copper methylpropyldithiocarbamate, copper methylbutyldithiocarbamate, copper methylpentyldithiocarbamate, copper methylhexyldithiocarbamate, copper methylphenyldithiocarbamate, copper ethylpropyldithiocarbamate, copper ethylbutyldithiocarbamate, copper ethylpentyldithiocarbamate, copper ethylhexyldithiocarbamate, copper ethylphenyldithiocarbamate, copper propylbutyldithiocarbamate, copper propylpentyldithiocarbamate, copper propylhexyldithiocarbamate, copper propylphenyldithio-carbamate, copper butylpentyldithiocarbamate, copper butylhexyldithiocarbamate, copper butylphenyldithiocarbamate, copper pentylhexyldithiocarbamate, copper pentylphenldithiocarbamate, and copper hexylphenyldithiocarbamate may be cited. These copper dialkyldithiocarbamates may be a monovalent copper salt or a divalent copper salt. Among other copper dialkyldithiocarbamates cited above, copper dimethyldithiocarbamate, copper diethyldithiocarbamate, and copper dibutyldithiocarbamate prove favorable in respect of its effects and easy acquisition, and copper dibutyldithiocarbamate proves especially favorable.

As typical examples of the manganese salt compound, manganese dialkyldithiocarbamates (wherein the two alkyl groups may be identical or different and each may be methyl, ethyl, propyl, or butyl), manganese diphenyldithiocarbamate, manganese formate, manganese acetate, manganese octanoate, manganese naphthenate, manganese permanganate, and manganese salt compounds of ethylenediamine tetraacetic acid may be cited. These manganese salt compounds may be used either singly or in the form of a mixture of two or more members.

This invention prefers the absorbing solvent to contain one or more compounds selected from the group consisting of N-oxyl compounds, phenol compounds, manganese salts, copper dialkyldithiocarbamates, nitroso compounds, and amine compounds or one or more compounds mentioned above in combination with phenothiazine. Naturally, when the absorbing solvent can be prepared as a system of three or more components by the addition of one or more of these six kinds of compounds and phenothiazone compound, it will manifest an effect in inhibiting polymerization equal to or better than the effect produced in a two-component system.

The amount of the polymerization inhibitor to be used does not need to be particularly restricted but may be properly selected to suit the operating conditions to be involved. It is preferable to set the total amount of the polymerization inhibitor to be used in the range of 3-3500 ppm (by mass) based on the mass of the acrylic acid in the reaction gas to be absorbed. As regards the preferred amount of the individual polymerization inhibitor to be used, this amount of the N-oxyl compound is in the range of 1-500 ppm based on the mass of the acrylic acid in the reaction gas, that of the manganese salt compound or the copper salt compound is in the range of 1-200 ppm based on the mass of the acrylic acid in the reaction gas, that of the nitroso compound is in the range of 1-500 ppm, that of the phenol compound is in the range of 1-500 ppm, that of the phenothiazine compound is in the range of 1-500 ppm, that of N-hydroxy-2,2,6,6-tetramethyl piperidine compound is in the range of 1-500 ppm, and that of 2,2,6,6-tetramethylpiperidine compound is in the range of 1-500 ppm.

In this invention, the polymerization inhibitor is preferred to be introduced into the reaction system in the form of a solution having the polymerization inhibitor dissolved in a solvent, namely in the form of a polymerization inhibitor-containing solution. The site for supplying the polymerization inhibitor-containing solution and the method for the introduction thereof do not need to be particularly restricted. The solution may be introduced into the absorption column at any stage other than the stage for supply of the raw material and the stage for supply of the reflux to the distilling column. In the absorption column, the "stage for supply of the raw material" means a stage for supplying an acrylic acid-containing gas and the "stage for supply of the reflux" means a stage for supplying a absorbing solvent. When the polymerization inhibitor is mixed with a solvent to prepare a polymerization inhibitor-containing solution and then this solution is to be supplied, the polymerization inhibitor is consumed effectively because it is uniformly dispersed in the acrylic acid absorption column. As the solvent for the preparation of the solution mentioned above, the acrylic acid-containing solution is available. When the absorbing solvent 21 which is used in the acrylic acid absorption column 20 contains acrylic acid, for example, the absorbing solvent 21 itself, part of the crude acrylic acid obtained in other process, a solution resulting from the thermal decomposition of an acrylic acid oligomer to be described specifically hereafter, or a bottom liquid of the absorption column may be used as an acrylic acid-containing solution. In the absorption column 20, it is particularly favorable to use waste liquid from a steam ejector used in the process for the production of acrylic acid as the acrylic acid-containing solution. This is because the waste liquid from the steam ejector is an aqueous solution containing acrylic acid, which has nearly the same composition ratio as that of the liquid inside the absorption column and induces no decrease in the absorption efficiency in the absorption column. If the acrylic acid-containing solution to be used has a higher acrylic acid concentration than the acrylic acid composition in the absorption column, this excess would possibly result in decreasing the absorption efficiency or induce polymerization.

The conditions for the operation of the absorption column 20 vary with such factors as the temperature of the acrylic acid-containing gas to be supplied to the absorption column, the amount of the gas supplied per unit time, and the volume of the absorption column. Generally, the temperature of the top of the absorption column is in the range of 40-85° C. If this temperature is lower than 40° C., the shortage would be at a disadvantage in necessitating plant investment for cooling and entailing consumption of cooling energy, increasing the condensation of a substance having a lower boiling point than acrylic acid, and consequently degrading the purity of acrylic acid in the bottom liquid of the absorption column. Conversely, if the temperature exceeds 80° C., the excess would result in increasing the loss of acrylic acid through the top of the absorption column and possibly lowering the yield of product.

The pressure at the top of the absorption column 20 is in the range of 0-30 kPa (gauge pressure). If this pressure is lower than 0 kPa (gauge pressure), the shortage would result in necessitating a vacuum device and entailing plant investment and cost of energy. If the pressure exceeds 30 kPa (gauge pressure), the excess would be at a disadvantage in necessitating a big capacity blower used for supplying a raw material gas to a reactor for catalytic gas phase oxidation and consequently entailing plant investment and cost of energy. When an exhaust gas from the top of the column is circulated to the reactor 10, diluting gas and unaltered raw material components can be effectively utilized.

In this invention, the aforementioned adjustment is preferred to set the amount of the liquid wetting the absorption column per cross-sectional area of the column at a level of not less than 0.3 $m^3/m^2 \cdot h$, preferably not less than 1 $m^3/m^2 \cdot h$. The term "amount of wetting liquid" is referred to as a value obtained by dividing the amount of the liquid [$m^3$] supplied per unit time onto one shelf by the cross-sectional area of the column. When this condition is satisfied, the interior of the absorption column is infallibly given a wetted state and the amount of the wetting liquid proves proper. Since the liquid is stored in a proper amount on the gas-liquid contact device, the state of the column wetted with the liquid and the state of the column avoiding drift and stagnation of gas or liquid can be both realized without fail.

The bottom liquid of the absorption column 20 is cooled with a cooler (not shown) annexed to the bottom part of the column and then circulated to the absorption column to increase the concentration of acrylic acid in the bottom liquid. Generally, in the bottom liquid of the absorption column 20, namely the aqueous acrylic acid-containing solution, such by-products as propylene remaining in an unaltered state, such by-products as formaldehyde, acrolein, furfural, benzaldehyde, formic acid, acetic acid, maleic acid, and acrylic acid oligomer, and additives such as polymerization inhibitor are present in addition to acrylic acid.

In this invention, the aqueous acrylic acid-containing solution mentioned above is led to the azeotropic dehydration column 30 and subjected, in conjunction with an azeotropic solvent supplied thereto, to azeotropic distillation. Subsequently to the process for obtaining the aqueous acrylic acid-containing solution, this invention prefers to install a tank and/or a cooler to cool the substance destined to be transferred to the subsequent process before the subsequent process is carried out. For example, the aqueous acrylic acid-containing solution, when necessary, is supplied to a distillation column 22 and deprived of such low boiling substance as acrolein therein, then the bottom liquid of the column is transferred via a pump 23 to a cooler 24, and the aqueous acrylic acid-containing solution which has been cooled herein is stored in a tank 25. By cooling this solution before it is transferred to the tank 25, it is made possible to cool the solution infallibly, decrease the retention time in the high-temperature state, and repress the amount of an oligomer to be formed. Optionally, the bottom liquid of the absorption column may be transferred to the tank without being passed through the distillation column 22, transferred via the pump 23 to the cooler 24, and then circulated to the tank 25 and transferred to the subsequent process as well. As typical examples of the cooler, shell-and-tube type heat exchangers, plate type heat exchangers, and spiral type heat exchangers which have been heretofore known to the art may be cited. Low boiling substances which can be removed in the distillation column 22 can be removed even in the azeotropic dehydration column 30. The separation of such low boiling substance can be effected as with a light-ends cut column which is separately installed. In this respect, the aqueous acrylic acid-containing solution contemplated by this invention broadly involves the water-containing acrylic acid prior to the transfer to the azeotropic dehydration column or the light-ends cut column and equals to the bottom liquid of the absorption column and the bottom liquid of the column obtained after the subsequent distillation. The cooling temperature for the aqueous acrylic acid-containing solution in the tank is preferred to be in the range of 20-50° C. Then, the aqueous acrylic acid-containing solution in the tank 25 is supplied to the azeotropic dehydration column 30.

As the azeotropic dehydration column 30, such known columns as plate column, packed column, wetted wall column, and spray column are usable. The azeotropic column 30, similarly to the absorption column 20 mentioned above, is generally preferred to be a plate column or a packed column. Incidentally, the preferred number of theoretical plates in the azeotropic dehydration column 30 is in the range of 3-30.

As typical examples of the azeotropic solvent to be used in this invention, solvents containing at least one member selected from the group consisting of heptane, dimethyl cyclohexane, ethyl cyclohexane, toluene, ethyl benzene, chlorobenzene, xylene, and mixtures thereof;

solvents containing at least one member selected from the group consisting of diethyl ketone, diisopropyl ketone, methylpropyl ketone, methylisobutyl ketone, methyl-t-butyl ketone, n-propyl acetate, n-butyl acetate, ethyl acrylatae, methyl methacrylate, ethyl methacrylate, vinyl acrylate, n-propyl acrylate, allyl acetate, isopropenyl acetate, vinyl propionate, propyl propionate, methyl crotonate, methyl valeate, ethyl butyrate, dibutyl ether, and mixtures thereof; and mixed solvents formed of a solvent containing at least one member selected from the group consisting of heptane, dimethyl cyclohexane, ethyl cyclohexane, toluene, ethyl benzene, chlorobenzene, xylene, and mixtures thereof with a solvent containing at least one member selected from the group consisting of diethyl ketone, diisopropyl ketone, methylpropyl ketone, methylisobutyl ketone, methyl-t-butyl ketone, n-propyl acetate, n-butyl acetate, ethyl acrylatae, methyl methacrylate, ethyl methacrylate, vinyl acrylate, n-propyl acrylate, allyl acetate, isopropenyl acetate, vinyl propionate, propyl propionate, methyl crotonate, methyl valeate, ethyl butyrate, dibutyl ether, and mixtures thereof may be cited.

More preferably, solvents containing at least one member selected from the group consisting of heptane, toluene, and mixtures thereof; solvents containing at least one member selected from the group consisting of ethyl methacrylate, methylisobutyl ketone, n-propyl acrylate, n-butyl acetate, and mixtures thereof; and a mixed solvent formed of a solvent containing at least one member selected from the group consisting of heptane, toluene, and mixtures thereof with a solvent containing at least one member selected from the group consisting of ethyl methacrylate, methylisobutyl ketone, n-propyl acrylate, n-butyl acetate, and mixtures thereof may be cited.

The amount of the azeotropic solvent to be used cannot be uniquely defined because it is fixed by such factors as the water content of the aqueous acrylic acid-containing solution supplied to the azeotropic dehydration column and the kind of azeotropic solvent to be used. It can be used at the known proportion adopted for the purpose of azeotrope. The amount of the azeotropic solvent is preferred to be large particularly from the viewpoint of preventing polymerization of acrylic acid. If it is unduly large, however, the excess would be at a disadvantage in necessitating a large amount of energy for distillation.

The temperature of the top of the azeotropic dehydration column 30 may be properly selected, depending on such factors as the water content and the amount of by-product present in the aqueous acrylic acid-containing solution to be supplied, the amount of feed liquid per unit time, the temperature of the feed liquid, the degree of dehydration aimed at, the kind of other component to be separated and the content thereof, and the kind of distillation column incorporated in the process for purifying acrylic acid. Generally, the pressure at the top of the column is in the range of 20-200 hPa (abs.) and the temperature of the top of the column is decided by the azeotropic composition which is proper for this operating pressure. The operation of the azeotropic dehydration column 30 is rendered efficient by providing it with an oil-water separator, introducing the distillate from the top of the column into the oil-water separator, separating the distillate into an oil phase (azeotropic solvent phase) 31 and a water phase 32, refluxing the oil phase 31 at a reflux ratio in the range of 0.5-10 to the azeotropic dehydration column 30, and circulating the water phase 32 to the absorption column 20 and used therein as the absorbing solvent 21. Consequently, the bottom liquid of the azeotropic dehydration column 30 acquires a composition having a water content of not more than 0.05 wt. % and an acetic acid concentration in the range of 0.02-3 wt. %.

The azeotropic dehydration column 30 prefers proper addition thereto of a polymerization inhibitor for the purpose of preventing acrylic acid from undergoing unwanted polymerization. As the polymerization inhibitor, the typical examples cited in the paragraph dealing with the absorption column 20 may be used either singly or in the form of a mixture of two or more members.

This invention prefers the polymerization inhibitor to be supplied in conjunction with acrylic acid. While water and the solvent are vaporized in the part of the distillation column above the stage for supply, acrylic acid escapes the vaporization and transfers to the bottom side of the column. Thus, the presence of acrylic acid is considered to be effective in preventing the polymerization inhibitor from being precipitated because the acrylic acid entrains the polymerization inhibitor. When the product of the thermal decomposition of the acrylic acid oligomer which will be described specifically herein below is used as the acrylic acid, it serves as an effective utilization of acrylic acid and contributes to the improvement of the productivity. When the acrylic acid is supplied to the azeotropic dehydration column 30, it will be at an advantage in enhancing the quality of product and preventing the polymerization inhibitor from being precipitated. It is inferred that while the by-produced maleic acid, when absorbed in water, is present in the aqueous solution in the form of hydrous maleic acid, it is gradually anhydridized when heated by repeating the work of distillation. Also in the acrylic acid recovered by the thermal decomposition, the water formed by this anhydridization is contained. By circulating this water to the azeotropic dehydration column and dehydrating it therein, therefore, it is made possible to lower the water content in the product. This dehydration process is at a further advantage in preventing the polymerization inhibitor from undergoing precipitation. According to this invention, the efficiency of production can be further improved by repressing the concentration of the acrylic acid oligomer (acrylic acid dimer and trimer) in the bottom liquid of the azeotropic dehydration column to a level of not more than 5 wt. %, more preferably to a level of not more than 3 wt. %.

Though the treatment of azeotropic dehydration removes water and low boiling substance contained in the aqueous acrylic acid-containing solution, the process for hydration and the process for separation of the low boiling substance may be carried out separately of each other. Generally, after the treatment for dehydration, the product by this dehydration can be refined by performing the process for the separation of high boiling substance either alone or in combination with other heretofore known method for purification. Not solely by distillation, the purification of acrylic acid may be effected by crystallization. Owing to the wide range allowed for the selection of a process of purification, this invention designates what is obtained by removing water and low boiling substances from the aqueous acrylic acid-containing solution as the crude acrylic acid and transfers it to the process for separation of high boiling substance.

In this invention, it is preferable to install a cooler or a tank between the process for azeotropic dehydration and/or the process for separation of low boiling substance and the process for separation of high boiling substance to cool the crude acrylic acid. The crude acrylic acid is cooled by transferring the bottom liquid with a pump 34 to a cooler 35 and the crude acrylic acid cooled therein is stored in a tank 36. By this transfer similarly to the transfer to the tank 25, it is made possible to cool the liquid infallibly by the cooling, decrease the time of retention in the high temperature part, and repress the amount of an oligomer suffered to occur. The cooling temperature of the crude acrylic acid in the tank 36 is preferred to be in the range of 20-50° C. As the cooler, shell-and-tube type heat exchangers, plate type heat exchangers, and spiral type heat exchangers which have been heretofore known to the art are usable. Then, the crude acrylic acid in the tank 36 is supplied to a heavy-ends cut column 40. The heavy-ends cut column 40 constitutes a process for heating the liquid under treatment and expelling acrylic acid by distillation through the top of a distillation column. From the viewpoint of the thermal efficiency, the feed liquid to the column 40 is preferred to have as high a temperature as permissible. If the temperature of the crude acrylic acid is unduly high, the excess of temperature would result in increasing the speed of oligomer formation, enlarging the possibility of polymerization, rendering easy the occurrence of a polymer in the heavy-ends cut column, degrading the final yield of acrylic acid, and possibly hindering the continuous operation in consequence of the occurrence of a polymer. If the temperature falls short of 20° C. and approximates closely to the freezing point, the shortage would be at a disadvantage in possibly freezing the content of the column and increasing the amount of heat to be applied during the process for the removal of high boiling substance. In consideration of the final efficiency of production based on the comparison with the amount of a polymer suffered to occur and the thermal efficiency, this invention has elected to cool the treated liquid between the subsequent processes. In the present invention, the yield can be improved at a highest level by cooling the treated liquid between the treatment for azeotropic dehydration and the treatment of high boiling substance.

As the heavy-ends cut column 40, such known columns as plate column, packed column, wetted wall column, and spray column are usable. The heavy-ends cut column, similarly to the azeotropic dehydration column mentioned above, is generally preferred to be a plate column or a packed column. These columns may contain a packing or stepped plates. The number of theoretical plates is in the range of 3-30, preferably 5-20.

The distillation in the heavy-ends cut column 40 may be performed under the conditions of distillation which have been heretofore known to the art. Specifically, the pressure at the top of the column is in the range of 20-200 hPa (abs.) and the temperature of the bottom of the column is not higher than 120° C.

The heavy-ends cut column 40, similarly to the azeotropic dehydration column 30 mentioned above, prefers addition thereto of a proper amount of polymerization inhibitor with the object of preventing acrylic acid from undergoing unwanted polymerization.

In this invention, the polymerization inhibitor is preferred to be introduced to any of the distillation columns at a stage other than the stage for supply of the raw material or the stage for supply of the reflux. More preferably, a polymerization inhibitor which conforms to the composition of the content of the column is injected at any of the stages which is present away from the stage for supply of the raw material and before the stage for supply of the reflux. Specifically, the polymerization inhibitor is supplied in conjunction with the acrylic acid-containing solution by an atomizing means through one or more spraying nozzles disposed in advance in the distilling column. The reason for the atomization is that it enables the solution containing the polymerization inhibitor to be sprayed in a wide range inside the distillation column and allows the polymerization to be prevented effectively. Even when the injection is made at the stage for supply of a raw material or the stage for supply of a reflux, the polymerization inhibitor may be injected as separated from the raw material and the reflux through another spraying nozzle or the polymerization inhibitor may be mixed in advance with the raw material and the reflux and the resultant mixture is injected through the spraying nozzle. Since the acrylic acid concentration does not vary very much in the heavy-ends cut column, the polymerization inhibitor may be supplied at a stage other than the stage for supply of the raw material and the stage for supply of the reflux or it may be injected at the stage for supply of the raw material and/or the stage for supply of the reflux. In this case, it is preferable to use as the acrylic acid part of the distillate obtained through the top of the column. The reason for the use of part of the distillate is that since the heavy-ends cut column is a device for obtaining acrylic acid, the use of the distillate substantially identical in quality with the product (raw material as ester and high purity acrylic acid) results in stabilizing the quality of product.

In this invention, it is permissible to condense the acrylic acid-containing distillate gas obtained through the top of the heavy-ends cut column 40 and supply at least part of the resultant acrylic acid-containing condensate liquid to the azeotropic dehydration column 30. Incidentally, the condensate liquid generally is a finished product of acrylic acid used as the raw material for the ester and high purity acrylic acid and the bottom liquid of the column contains the polymerization inhibitor, acrylic acid oligomer, and other high boiling substances. In this invention, the bottom liquid is designated as a high boiling substance-containing solution and is subjected to a process for thermally decomposing the acrylic acid oligomer contained therein and consequently recovering acrylic acid.

The thermal decomposition of the acrylic acid oligomer is carried out in a thermal decomposition tank 51. The thermal decomposition tank 51 does not need to be particularly discriminated on account of its form. Since the oligomer has high viscosity, possibly shows precipitation of a solid substance, and displays an inferior liquid property, the tank is preferred to be endowed with an inclination toward the liquid outlet and provided with a liquid circulating and/or stirring device capable of uniformizing the composition inside the tank. The concentration of maleic acid contained in the decomposed liquid obtained by the thermal decomposition is set so as to be not more than 5 wt. %, preferably in the range of 0-3 wt. %, and more preferably in the range of 0-1 wt. %. The reason for restricting the malic acid concentration to not more than 5 wt. % is that the maleic acid readily converts into fumaric acid which is an isomer and the fumaric acid having a high melting point precipitates as a solid.

For the purpose of obtaining the decomposed liquid of this description, it is preferred to provide the decomposition tank 51 in the lower part thereof with a distilling device such as, for example, a maleic acid separation column 46. The high boiling substance-containing solution is supplied to the maleic acid separation column 46, the bottom liquid of the column is concentrated with a thin film evaporator 50, and the oligomer is decomposed in the thermal decomposition tank 51. The liquid obtained from the thermal decomposition tank 51 may be again concentrated in the thin film evaporator 50 and the acrylic acid obtained in consequence of the thermal decomposition may be recovered. Since the acrylic acid is vaporized in the thin film evaporator 50, this acrylic acid may be recovered through the top of the maleic acid separation column 46.

The maleic acid separation column 46 has a number of theoretical plates of 1-10, preferably 1-5. The distillation in this column is preferred to be performed at a column top pressure in the range of 10-150 hPa (abs.) and a column bottom temperature of not higher than 120° C. The thin film evaporator 50 is preferred over a shell-and-tube type heat exchanger in respect that it is capable of concentrating even a liquid of high viscosity. This device does not need to be discriminated between a horizontal type and a vertical type.

The thermal decomposition temperature in the thermal decomposition tank 51 is generally in the range of 120-220° C. and particularly preferably in the range of 120-160° C. While the retention time (amount of liquid reserved in the thermal decomposition tank/amount of waste oil) is not generally defined because it varies with the temperature of thermal decomposition, it is generally required to be in the range of 20-50 hours. Thus, the thermal decomposition tank 51 needs to provide with a heating means. It suffices, however, to maintain the temperature of the thermal decomposition by externally jacketing the tank and/or internally (or externally) disposing a heat exchanger and utilizing such a heat medium as steam or oil.

This invention permits addition of a polymerization inhibitor to the high boiling substance-containing solution prior to subjecting this solution to thermal decomposition in the maleic acid separation column 46, the thin film evaporator 50, or the thermal decomposition tank 51. This addition results in efficiently preventing the polymerization and possibly promoting the thermal decomposition. As the polymerization inhibitor capable of promoting the thermal decomposition, 4,4',4"-tris-(2,2,6,6-tetramethyl piperidinoxyl)phosphite and one or more of the compounds, namely, 2,2,6,6-tetramethyl piperidinoxyls represented by the following formula (1):

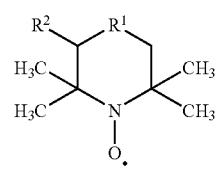

(1)

(wherein $R^1$ stands for $CH_2$, $CHOH$, $CHCH_2OH$, $CHCH_2CH_2OH$, $CHOCH_2OH$, $CHOCH_2CH_2OH$, $CHCOOH$, or $C=O$ and $R^2$ stands for a hydrogen atom or $CH_2OH$), one or more of the N,hydroxy-2,2,6,6-tetramethyl piperidine compounds such as, for example, 1,4-dihydroxy-2,2,6,6-tetramethyl piperidine and 1-hydroxy-2,2,6,6-tetramethyl piperidine, and 2,2,6,6-tetramethyl piperidine compounds such as, for example, 2,2,6,6-tetramethyl piperidine and 4-hydroxy-2,2,6,6-tetramethyl piperidine may be used in combination among other examples cited above.

In this invention, the acrylic acid which is recovered by thermally decomposing the oligomer mentioned above is preferred to be supplied to the process for dehydration. This is because the purification by elimination of such impurities as water to be contained in the subsequent process will be attained and the polymerization inhibitor will be put to effective utilization. To be specific, the dehydration proves favorable, both in terms of lowering the water content in the product thereby heightening the quality of the product and preventing the polymerization inhibitor from being precipitated.

Incidentally, the acrylic acid expelled by distillation through the top of the heavy-ends cut column 40 is enabled to produce an acrylic ester when it is supplied to a process for the production of the acrylic ester.

Now, a method for producing an acrylic ester from acrylic acid will be explained below as one mode of embodying this invention.

To an esterification reactor 60 packed with a strongly acidic cation-exchange resin as a catalyst, the acrylic acid obtained in the heavy-ends cut column 40 is supplied and then an alcohol and other are charged to the reactor 60 to form an ester. Then, the reaction solution is introduced into an acid separation column 80, which by distillation expels an acrylic ester, unaltered alcohol, water, and other low boiling substance through the top thereof. Subsequently, the distillate emanating from the top of the acid separation column 80 is introduced into an oil-water separator and is separated therein into an oil phase 81 containing an acrylic ester and a water phase 82 having water and alcohol as main components. The water phase 82 is transferred to an alcohol recovery column 90 like a water phase 72 in the oil-water separator which is the distillate through the top of the water-separation column 70, and the oil phase 81 is supplied to a light-ends cut column 100. In this while, part of the oil phase 81 may be refluxed to the acid separation column 80. In the light-ends cut column 100, the acrylic ester is separated through the bottom and supplied to a refining column 110 and the produced acrylic ester 111 is expelled by distillation through the top. Incidentally, the alcohol which has been expelled by distillation through the top of the alcohol recovery column 90 may be circulated to the oil phase 81 in the oil-water separator annexed to the acid separation column 80. The water, alcohol, and other low boiling substances expelled by distillation through the top of the light-ends cut column 100 are circulated to the esterification reactor 60 through the column provided in the upper part of the esterification reactor 60.

In this process for the production of an acrylic ester, the bottom liquid of the acid separation column 80 eventually contains acrylic acid dimer and acrylic acid dimer ester and Michael type adducts such as alkoxypropionic acids and alkoxypropionic esters represented by the following formula [II] together with the raw material components such as acrylic acid.

$$R^1-O-(-X-COO)_m-R^2 \qquad [II]$$

(wherein m is an integer in the range of 1-5, $R^1$ and $R^2$ independently stand for a hydrogen atom or an alkyl group, and —X— stands for —$CH_2CH_2$— or —$CH(CH_3)$—, providing that when m is not less than 2, a plurality of —X—'s may be identical or different).

Thus, the bottom liquid of the acid separation column 80 may be circulated to the esterification reactor 60 as illustrated in FIG. 1 or it may be supplied to a separately provided thin film evaporator and decomposition tank (not shown) to decompose the acrylic acid oligomer contained therein. The components contained in the bottom liquid are decomposed and further converted in the thin film evaporator into an alcohol, acrylic acid, and an acrylic acid ester. When these components are introduced again into the esterification reactor 60, they constitute effective utilization of components. Incidentally, the decomposition of the bottom liquid may be promoted by the addition of the aforementioned N-oxyl compound.

The method for the production of an acrylic ester consists in obtaining an ester by subjecting acrylic acid and an alcohol to a reaction of dehydration. As typical examples of the preferred alcohol, various species of alcohol such as methanol, ethanol, n-butanol, isobutanol, sec-butanol, t-butanol, 1-pentanol, 2-pentanol, 3-pentanol, cyclopentanol, 1-hexanol, 2-hexanol, 3-hexanol, cyclohexanol, 1-heptanol, 2-heptanol, 3-heptanol, 1-octanol, isooctanol, 2-ethylhexanol, isononyl alcohol, and lauryl alcohol may be cited. They may be in a linear form or in a branched form. They may be used either singly or in the form of a combination of two or more members. Incidentally, the reaction conditions and distillation conditions for each of the processes mentioned above may be arbitrarily selected from the known conditions.

The acrylic acid which is obtained from the heavy-ends cut column 40 may be further refined as with a distillation column to obtain acrylic acid of high purity. For example, a conventional primary amine such as hydrazine hydrate and phenyl hydrazine and/or the salts thereof is added to the acrylic acid in an amount in the range of 1.0-10.0 moles, preferably 1.0-5.0 moles, per mol of the aldehyde contained therein, and after a treating agent is further added thereto, the resultant mixture is subjected to vacuum distillation with a known distillation column. This distillation is performed, for example, in a flash column fitted with a mist separator under a column top pressure in the range of 10-150 hPa (abs.) at a column top temperature in the range of 35-90° C. By this treatment, the concentrations of such aldehydes as furfural, acrolein, and benzaldehyde can be decreased to less than 10 ppm. Acrylic acid of equal purity can be obtained by using a crystallization device. When a water-absorbent resin is produced from acrylic acid, it possibly proves unfavorable for a given use because of its odor or stimulus to the skin. Acrylic acid of high purity obtained by such purification can be preferably used in this case. In this invention, the acrylic acid of high purity thus obtained is supplied to a polyacrylic acid (salt) production process 120 to produce polyacrylic acid (salt), which may be used to produce a water-absorbent resin, for example.

When polyacrylic acid is produced from acrylic acid of high purity, this invention prefers the purified acrylic acid to be transferred with the pump 42 to the cooler 43 and the acrylic acid cooled in the cooler 43 to be stored in the tank 44. The reason for commending this process is that by this cooling, it is made possible to cool the liquid infallibly, decrease the retention time in the high temperature part, and repress the amount of the oligomer suffered to form. The cooling temperature of acrylic acid in the tank is preferred to be in the range of 20-50° C.

The polyacrylic acid (salt) production process 120 is capable of producing polyacrylic acid (salt) by sequentially introducing the acrylic acid mentioned above to a neutralization process 121, a polymerization process 122, a drying process 123, and a cooling process 124 and subjecting it to the relevant treatments therein. When acrylic acid is not neutralized, polyacrylic acid is obtained. The neutralization process mentioned above is performed optionally. The acrylic acid may be given a treatment adapted to improve a varying physical property. A cross-linking process may be additionally performed during or after the polymerization process.

The neutralization process is an arbitrary additive process. For example, a method which comprises mixing acrylic acid or a produced polyacrylic acid (salt) with a prescribed amount of a powder or aqueous solution of a basic substance may be cited. This method does not need to be particularly restricted but may be properly selected from the known methods. This neutralization process may be carried out prior to polymerization (neutralized in the form of a monomer), during the polymerization, or after the polymerization (neutralized in the form of a gel), or both before and after the polymerization. Though the diagram depicts a process which performs polymerization after neutralization, the neutralization may be performed, when necessary, after the polymerization. In this case, the configuration of equipment and the sequence of component processes may be properly altered to suit the occasion. A polymerization device and a neutralization device may be identical or different.

The basic substance to be used for neutralizing acrylic acid may be properly selected among the known basic substances such as, for example, (hydrogen) carbonates, hydroxides of alkali metals, ammonia, and organic amines. The radio of neutralization of acrylic acid does not need to be particularly restricted but may be properly selected in the range of 30-100 mol % and preferably 50-80 mol %. When the heat of reaction which is generated during the neutralization is required to be removed, it suffices to introduce the product emitting the heat of reaction into a proper cooling means such as, for example, a cooling device represented by a cooling tower.

The acrylic acid salt solution resulting from the neutralization, when necessary, is introduced into a polymerization process. The method of polymerization in this process does not need to be particularly restricted. When the polymerization needs to use a radical polymerization initiator, it may be performed by any of the known methods of polymerization such as stripping polymerization, electron stripping polymerization, and photosensitized polymerization. In the polymerization process, acrylic acid may be neutralized as occasion demands and then subjected in the form of an aqueous solution of acrylic acid (salt) of a concentration preferably of not less than 10 wt. %, more preferably not less than 20 wt. % and preferably of not more than 80 wt. %, more preferably not more than 70 wt. %.

This invention allows various conditions such as the kind of polymerization initiator and the conditions for polymerization to be arbitrarily selected. Optionally, various known additives such as cross-linking agent, other monomer, and even water-soluble chain transfer agent, and hydrophilic macromolecular substance may be added. For the polymerization process, reactors and devices selected arbitrarily may be used. Any of the polymerization devices in common use may be used without any particular restriction.

The polyacrylic acid (salt) resulting from the polymerization is generally a polymer of the form of a hydrogel and, therefore, is further subjected to a drying process for the purpose of removing water. The method for this drying does not need to be particularly restricted. The polymer may be dried with any of the known drying devices such as hot air drier, fluidized bed drier, drum drier, and Nauter type drier at a proper drying temperature preferably in the range of 70-230° C. As the heat medium to be supplied to a drying process 123, the vapor discharged in the process for the production of acrylic acid, particularly the heat of reaction emitted from the catalytic gas phase oxidizer may be utilized.

The hydrogel, namely the hydrous polymer, of polyacrylic acid (salt) is thermally dried with a varying type of drier. The drying may be attained, for example, by exposing the hydrogel to the heating surface of such a conducting heat transfer drier as a drum drier or a paddle drier which has been heated with steam. From the viewpoint of decreasing the residual monomer content and exalting the drying efficiency, the hot air transfer drying which expose the hydrogel directly to the steam proves particularly preferable. Preferably, the hydrogel is dried with a steam-containing gas such as, for example, a hot air having a dew point preferably of not lower than 50° C., more preferably not lower than 60° C. and preferably not higher than 90° C., more preferably not higher than 80° C. and having a temperature preferably of not lower than 100° C., and more preferably not lower than 150° C. and preferably not higher than 200° C., more preferably not higher than 180° C. because this drying promotes the decrease of the residual monomer content and the exaltation of the water-absorption ratio of the polyacrylic acid (salt). Incidentally, the duration of drying is generally in the range of one minute to three hours, preferably five minutes to one hour.

The polyacrylic acid (salt) which is obtained after the drying process is still hot at the time of its release from the drying device. Preferably, therefore, it is cooled in a cooling process 124 at a suitable temperature in the range of room temperature to 90° C., preferably 40 to 80° C. The method for cooling this polyacrylic acid (salt) does not need to be particularly restricted. It may be cooled, for example, by being blown with cold air or introduced into such a cooling device as a refrigerator.

The polyacrylic acid (salt) which has been cooled to a prescribed temperature may be put to use in its unaltered form. Optionally, it may be further molded in a prescribed shape as by granulation or pulverization and then made to incorporate therein various additives such as reducing agent, flavoring agent, and binder so as to suit the purpose of application.

This invention prefers the dried polyacrylic acid (salt) to be cooled. When the hydrogel is finely divided to a particle size in the approximate range of one-several mm and dried, the dried polyacrylic acid (salt) is in the form of dry particles measuring about one-several mm. Generally, the dried particles assume the form of an agglomerate. Thus, the dried polyacrylic acid (salt) may be optionally pulverized or further classified to obtain a polyacric acid (salt) powder having a weight average particle diameter in the range of 10-1000 μm, preferably 100-800 μm. When this powder and various modifying agents such as, for example, an aqueous solution of a surface cross-linking agent, pelletizing binder, and deodorant are added together, the application of a cooling process enhances the efficiency of pulverization and sharpens the particle diameter distribution and allows the various modifying agents to be uniformly added to the powder. Thus, the cooling process in this case can exalt various physical properties of the water-absorbent resin such as, for example, a water-absorption ratio under pressure while restraining dispersion among individual particles of powder.

For this invention, it is preferable to introduce a polymerization inhibitor to any of the distillation columns at a stage other than the stage for supply of the raw material and the stage for supply of the reflux. Particularly, the site for supply of the polymerization inhibitor to the azeotropic dehydration column is preferred to be higher than the stage for supply of the raw material markedly different in composition and to be lower than the stage for supply of the reflux. The polymerization inhibitor in this case is preferred to be supplied together with the acrylic acid-containing solution by the use of an atomizing injection means. Particularly in the azeotropic dehydration column, the acrylic acid which is recovered by thermally decomposing an acrylic acid oligomer is used efficiently as the acrylic acid-containing solution.

EXAMPLES

Now, this invention will be more specifically described below with reference to working examples.

Example 1

Acrylic acid was produced by following the process flow illustrated in FIG. 1. First, by subjecting propylene to catalytic gas phase oxidation with a molecular oxygen in the presence of an oxidizing catalyst, a mixed gas containing 7.1 vol. % of acrylic acid, 0.3 vol. % of acetic acid, and 14.7 vol. % of water was obtained at a rate of 388 Nm$^3$/min.

This gas was introduced into an absorption column (cascade miniring 3P 10 m) to obtain a bottom liquid at a rate of 8050 kg/h. This absorption column was operated with the top thereof kept under 1100 hPa abs. at 62° C. Through the top of the column, water obtained by mixing hydroquinone as a polymerization inhibitor, separated water occurring in an azeotropic dehydration column, and waste water generated from a vacuum generating device in a distillation column and containing 1.5 wt. % of acrylic acid and 5.4 wt. % of acetic acid was supplied as a absorbing water at a rate of 2720 kg/h. Part of the exhaust gas emanating through the top of the column was circulated to an oxidation reactor and the remainder thereof was released as the waste gas from the system. The bottom liquid of the absorption column was further distilled to obtain an aqueous acrylic acid solution containing 70 wt. % of acrylic acid, 3.4 wt. % of acetic acid, and 0.3 wt. % of maleic acid.

The aqueous acrylic acid solution thus obtained was passed through a cooling device annexed to a tank interposed between the absorption column and the azeotropic dehydration column to be cooled to 40° C. and the cooled aqueous solution was supplied together with part of the liquid at the top of a maleic acid separation column to the middle stage of the azeotropic dehydrating column provided with 50 sieve trays.

The azeotropic dehydration column was operated under the conditions of 190 hPa abs. in column top pressure and 1.0 in reflux ratio (total number of moles of the reflux per unit time/total number of moles of the distillate per unit time) to effect azeotropic separation with toluene. The top liquid of the separation column was led together with the waste water from a steam ejector which was a vacuum generating device to a storage tank and separated therein into an organic phase and a water phase. As the polymerization inhibitor for the column, copper dibutyldithiocarbamate and hydroquinone monomethyl ether were dissolved in the reflux, then the resultant mixture was introduced into the column together with the reflux. And hydroquinone dissolved in water were injected by spraying into the column together with part of the top liquid of a maleic acid separation column containing the acrylic acid recovered by thermally decomposing the oligomer from a stage intervening between the stage for supply of an aqueous acrylic acid solution and the stage for supply of the reflux. The concentration of the acrylic acid oligomer (acrylic acid dimer and trimer) in the bottom of the column was found to be 2 wt. %.

The bottom liquid of the column was passed through a cooler annexed to a tank interposed between this column and a heavy-ends cut column to be cooled to 40° C. and then supplied to the heavy-ends cut column provided with 45 sieve trays through the intermediary stage thereof. This column was operated under the conditions of 45 hPa abs. in tower top pressure and 1.4 in reflux ratio. Through the top of the column, acrylic acid was obtained at a rate of 5120 kg/h. The bottom liquid of this column which contained 31 wt. % of acrylic acid oligomer and 5 wt. % of maleic acid was supplied to a maleic acid separation column provided with five sieve trays through the bottom thereof.

The column was provided in the bottom thereof with a thin film evaporator and a thermal decomposition tank and operated under the conditions of 45 hPa abs. in pressure and 0.5 in reflux ratio to obtain acrylic acid containing 0.5 wt. % of maleic acid at a rate of 400 kg/h through the top of the column. The acrylic acid thus obtained was used as the raw material for ester and high-purity acrylic acid. The high-purity acrylic acid was further used for the production of polyacrylic acid. Separately, the bottom liquid of the thin film evaporator was introduced into a thermal decomposition tank and subjected therein to thermal decomposition under the conditions of 150° C. in temperature and 40 hours in retention time. Part of the bottom liquid formed in the tank was circulated to the thin film evaporator. To the heavy-ends cut column and the maleic acid separation column, a solution of copper dibutyl dithiocarbamate and hydroquinone monomethyl ether in acrylic acid was introduced as a polymerization inhibitor by spraying to a condenser. The waste oil containing 5.5 wt. % of acrylic acid and 39 wt. % of acrylic acid oligomer (acrylic acid dimer and trimer) was discarded from the thermal decomposition tank at a rate of 170 kg/h. The plant was stopped after about three months' continued operation and then opened to test the interior. The test failed to detect any sign of problem. The results of working examples and a comparative experiment are shown in Table 1. In Table 1, (i) represents the case of injecting the polymerization inhibitor containing solution to stages other than the stage for supply of a raw material and the stage for supply of the reflux, (ii) the case of supplying the acrylic acid recovered by thermally decomposing the oligomer to the process of dehydration, (iii) the case of supplying the polymerization inhibitor containing solution together with an acrylic acid-containing solution with an atomizing injection means, and (iv) the case of adjusting the concentration of maleic acid contained in the acrylic acid solution recovered by thermally decomposing the oligomer contained in the high boiling substance-containing solution to below 5 wt. %. The symbol ○ represents actual application and the symbol – represents the absence of actual application.

Example 2

An operation was carried out by following the procedure of Example 1 while supplying hydroquinone dissolved in water together with an aqueous acrylic acid solution as part of the polymerization inhibitor to the azeotropic dehydration column at the stage for supply of the aqueous solution. The pressure loss in the azeotropic dehydration column showed a sign of rise in about one week's continued operation. When the plant was opened and tested after about two months' continued operation, the deposition of a polymer was found on the sieve trays higher than the stage for supply of the aqueous acrylic acid solution.

Example 3

An operation was performed by following the procedure of Example 1 while supplying hydroquinone as part of the polymerization inhibitor directly to the azeotropic dehydration column without using the top liquid of a maleic acid separation column. On the day following the start of the operation, the azeotropic dehydration column showed a sign of an increase in the pressure loss. When the plant was opened to check the interior thereof after about one month's continued operation, the precipitation of the polymerization inhibitor occurred in the neighborhood of the stage for introduction of the polymerization inhibitor into the column and the holes in the trays were found to be blockage.

Example 4

An operation was performed by following the procedure of Example 1 while supplying the polymerization inhibitor directly to the column without using the cooler annexed to the tank. As a result, the concentration of the acrylic acid oligomer (acrylic acid dimer and trimer) in the waste oil from the thermal decomposition tank increased to 43 wt. % and the amount of the waste oil was increased to 200 kg/h. When the plant was stopped after about three months' continued operation to test the interior thereof, no sign of trouble was detected.

Comparative Example 1

An operation was performed by following the procedure of Example 1 with the exception of the following modifications. First, hydroquinone as one of the components of the polymerization inhibitor supplied to the azeotropic dehydration column was dissolved in water and supplied together with the aqueous acrylic acid solution to the step for supply of the aqueous solution. The bottom liquid of the heavy-ends cut column was directly supplied to the thin film evaporator and the acrylic acid recovered from the evaporator was circulated to the heavy-ends cut column. Further, this process was directly shifted to the subsequent process without using the cooler annexed to the tank.

The maleic acid concentration in the acrylic acid recovered from the thin film evaporator was about 6 wt. %. Thus, the water content and the concentration of such high boiling substances as maleic acid in the acrylic acid were higher than those obtained in Example 1. The amount of the waste oil was 210 kg/h and the oligomer concentration in the waste oil was 43 wt. %. The azeotropic dehydration column began to show a discernible sign of rise of pressure on the day following the start of the operation. Though the operation could be continued for about one month, it had to be stopped owing to the rise of the pressure during the refining process. When the plant was opened to test the interior thereof, the azeotropic dehydration column was found to have a discernible sign of precipitation of the polymer and the polymer inhibitor. In the neighborhood of the heavy-ends cut column and the thin film evaporator, precipitation of fumaric acid inferred to be formed by the transfer of heat of the maleic acid and the polymer were confirmed.

The concentration of the acrylic acid oligomer (acrylic acid dimer and trimer) in the bottom of the azeotropic dehydration column was 6 wt. %.

Example 5

An operation was performed by following the procedure of Comparative Example 1 while introducing hydroquinone as the polymerization inhibitor to the azeotropic dehydration column at a stage between the stage for supply of the raw material and the stage for supply of the reflux. The plant was opened to test the interior thereof after one month's continued operation. Though the amount of the polymer suffered to occur in the azeotropic dehydration column was small as compared with Comparative Example 1, the precipitation of the polymerization inhibitor was found be occurred in the proximity of the site for injection of the polymerization inhibitor and blockage also was found in the holes in the trays. The neighborhood of the heavy-ends cut column and the thin film evaporator was not notably different from that in Comparative Example 1.

Example 6

An operation was performed by following the procedure of Comparative Example 1 while circulating the acrylic acid recovered from the thin film evaporator to the azeotropic dehydration column. When the plant was opened to test the interior thereof after one month's continued operation, the results of test were not notably different from those of Comparative Example 1. The water content of the produced acrylic acid, however, was decreased.

Example 7

An operation was performed by following the procedure of Comparative Example 1 while introducing hydroquinone as the polymerization inhibitor to the azeotropic dehydration column by spraying together with part of the acrylic acid obtained through the top of the heavy-ends cut column at the stage intervening between the stage for supply of raw material and the stage for supply of the reflux. The plant was opened one month's continued operation to test the interior thereof. Though the azeotropic dehydration column showed no sign of any particular problem, the results of test in the neighborhood of the heavy-ends cut column and the thin film evaporator were not notably different from those of Comparative Example 1.

TABLE 1

| Construction | Example 1 | Example 2 | Example 3 | Example 4 | Example 5 | Example 6 | Example 7 | Comparative Example 1 |
|---|---|---|---|---|---|---|---|---|
| (i) | ○ | — | ○ | ○ | ○ | — | ○ | — |
| (ii) | ○ | ○ | ○ | ○ | — | ○ | — | — |
| (iii) | ○ | ○ | — | ○ | — | — | ○ | — |
| (iv) | ○ | ○ | ○ | ○ | — | — | — | — |
| Cooling Treatment | ○ | ○ | ○ | — | — | — | — | — |
| Duration of operation | Not less than 3 months | Not less than 2 months | Not less than 1 month | Not less than 3 months | Not less than 1 month | Not less than 1 month | Not less than 1 month | One month |
| Time for Test | About 3 months | About 2 months | About 1 month | About 3 months | About 1 month | One month | One month | One month |
| [Results of Test] Azeotropic dehydration column | No problem | Polymer above stage for supply of aqueous solution | Precipitate near stage for introduction of polymerization inhibitor | No problem | Precipitate near stage for introduction of polymerization inhibitor | Polymer and precipitate | No problem | Polymer and precipitate |
| Heavy-ends cut column-thin film evaporator | No problem | No problem | No problem | No problem | Polymer (fumaric acid) | Polymer (fumaric acid) | Polymer (fumaric acid) | Polymer (fumaric acid) |
| Amount of waste oil | 170 kg/h | 170 kg/h | 170 kg/h | 200 kg/h | 210 kg/h | 210 kg/h | 210 kg/h | 210 kg/h |
| Product | Low water content and low concentration of high boiling substance | Low water content and low concentration of high boiling substance | Low water content and low concentration of high boiling substance | Low water content and low concentration of high boiling substance | Rise of water content and high boiling substance concentration | Decline of water content | Rise of water content and high boiling substance concentration | Rise of water content and high boiling substance concentration |

The invention claimed is:
1. A method for the production of acrylic acid which comprises the steps of:

(a) supplying one or more gas components selected from the group consisting of propylene, propane and acrolein to a reactor for catalytic gas phase oxidation, (b) obtaining an acrylic acid-containing gas by catalytic gas phase oxidation, (c) introducing said acrylic acid-containing gas and supplying an aqueous absorbing solvent into an acrylic acid absorbing column, whereby an aqueous acrylic acid-containing solution is absorbed onto said acrylic acid absorbing column (d) obtaining said aqueous acrylic acid-containing solution absorbed onto said acrylic acid absorbing column, (e) obtaining crude acrylic acid from said aqueous acrylic containing solution in an azeotropic dehydration column by dehydration;

(f) introducing a polymerization inhibitor to said azeotropic dehydration column at any point between a point for supplying said aqueous acrylic acid containing solution and a point for supplying a reflux and not including the point for supplying said aqueous acrylic acid containing solution material and the point for supplying the reflux;

(g) optionally removing a low boiling substance from said aqueous acrylic acid-containing solution by using an azeotropic distillation column, (h) obtaining acrylic acid and a high boiling substance-containing solution by removing the high boiling substance from said crude acrylic acid, subsequently (i) recovering acrylic acid by thermally decomposing an acrylic acid oligomer contained in said high boiling substance-containing solution, and (j) supplying the acrylic acid recovered by thermally decomposing said acrylic acid oligomer from step (i) to said azeotropic dehydration column.

2. A method according to claim 1, which further comprises performing the step of;

thermally decomposing the oligomer contained in said high boiling substance-containing solution thereby lowering a concentration of maleic acid contained in the recovered acrylic acid solution to a level of not higher than 5 wt. %.

3. A method according to claim 1, which further comprises the steps of;

(j) for esterfying the acrylic acid obtained in said step (i) thereby producing an acrylic ester, or (k) for further purifying the acrylic acid obtained in said step (i) thereby obtaining acrylic acid of high purity.

4. A method according to claim 3, further comprising the step of cooling the aqueous acrylic acid-containing solution in a tank and/or a cooler between said steps (b)-(k) and the subsequent step.

5. A method for the production of a polyacrylic acid or salt thereof characterized by producing said polyacrylic acid or salt by using the acrylic acid of high purity obtained at the step (k) set forth in claim 3 in a polymerization process.

6. A method according to claim 5, further comprising the step of cooling the aqueous acrylic acid-containing solution in a tank and/or a cooler between said step (k) and a step for producing the polyacrylic acid or salt.

7. A method for the production of a polyacrylic acid or salt thereof, characterized by producing said polyacrylic acid or salt by using the acrylic acid of high purity obtained at the step (k) set forth in claim 4 in a polymerization process.

8. A method according to claim 1, wherein said distillation column is at least one member selected from the group consisting of the azeotropic dehydration column, the heavy-ends cut column and the maleic acid separation column.

9. A method according to claim 1, wherein said distillation column is at least one member selected from the group consisting of the azeotropic dehydration column and the heavy-ends cut column.

10. A method according to claim 1, wherein said thermal decomposition of the acrylic acid oligomer to acrylic acid in the step (i) is carried out at a temperature of 120°-220° C.

11. A method according to claim 1, wherein said thermal decomposition of the acrylic acid oligomer is carried out in a thermal decomposition vessel.

* * * * *